(12) United States Patent
Piantoni et al.

(10) Patent No.: US 10,765,562 B2
(45) Date of Patent: Sep. 8, 2020

(54) APPARATUS FOR TRANSFERRING AND ROTATING AN OBJECT

(71) Applicant: GDM S.p.A., Bologna (IT)

(72) Inventors: Matteo Piantoni, Albino (IT); Valerio Soli, Bologna (IT); Marco Rosani, Vailate (IT); Federico Tordini, Treviglio (IT); Francesco Passarotto, Bologna (IT); Andrea Duchini, Castelleone (IT)

(73) Assignee: GDM S.p.A., Bologna (IT)

( * ) Notice: Subject to any disclaimer, the term of this patent is extended or adjusted under 35 U.S.C. 154(b) by 14 days.

(21) Appl. No.: 16/328,499

(22) PCT Filed: Aug. 1, 2017

(86) PCT No.: PCT/IB2017/054699
§ 371 (c)(1),
(2) Date: Feb. 26, 2019

(87) PCT Pub. No.: WO2018/037304
PCT Pub. Date: Mar. 1, 2018

(65) Prior Publication Data
US 2020/0222248 A1    Jul. 16, 2020

(30) Foreign Application Priority Data

Aug. 26, 2016   (IT) ........................ 102016000087583

(51) Int. Cl.
*A61F 13/15*         (2006.01)
*B65G 47/244*        (2006.01)
(Continued)

(52) U.S. Cl.
CPC ...... *A61F 13/15764* (2013.01); *B65G 47/244* (2013.01); *B65G 47/846* (2013.01);
(Continued)

(58) Field of Classification Search
CPC ...... B65G 47/32; B65G 47/846; B65G 29/00; B65G 47/848; B65G 47/84; B65G 47/47;
(Continued)

(56) References Cited

U.S. PATENT DOCUMENTS

| 5,025,910 A | 6/1991 | Lasure et al. |
| 7,975,584 B2 * | 7/2011 | McCabe ........... A61F 13/15723 53/462 |

(Continued)

FOREIGN PATENT DOCUMENTS

| CN | 101686890 A | 3/2010 |
| CN | 104670966 A | 6/2015 |

(Continued)

OTHER PUBLICATIONS

International Search Report and Written Opinion of the International Searching Authority Application No. PCT/IB2017/054699 Completed: Sep. 8, 2017; dated Sep. 19, 2017 13 pages.
Chinese Office Action Application No. 201780050471.5 dated Mar. 26, 2020, 5 pages.

*Primary Examiner* — James R Bidwell
(74) *Attorney, Agent, or Firm* — Whitmyer IP Group LLC (57) ABSTRACT

An apparatus transferring and rotating an object from a retaining station to a releasing station along an annular transfer path, the object has a first orientation in the retaining station which is different from a second orientation in the releasing station; the apparatus includes: a stator having a revolution body provided with a lateral surface on which a first cam profile is formed; a rotor that is rotatable about a first rotation axis with respect to the stator; at least one retaining head of the object connected to the rotor, which has a retaining element coupled to the first cam profile which can be rotated about a second axis of rotation with respect to the rotor; and wherein the stator has a second cam profile and the transferring and rotating apparatus has at least a first (Continued)

annular guide disposed along the transfer path and the head has at least one first slide supporting the retaining element and is slidably coupled to the first annular guide, the first slide being connected to the rotor by way of a respective angular position variation mechanism coupled to the second cam profile to induce the sliding of the first slide into the first annular guide.

20 Claims, 9 Drawing Sheets

(51) Int. Cl.
    *B65H 5/10*     (2006.01)
    *B65G 47/84*     (2006.01)

(52) U.S. Cl.
    CPC .............. *B65G 47/848* (2013.01); *B65H 5/10* (2013.01); *B65H 2701/1924* (2013.01)

(58) Field of Classification Search
    CPC ................................ B65G 47/244; B65H 5/10; B65H 2701/1924; B65B 9/00; A61F 13/15; A61F 13/15764; A61F 13/15804
    USPC ......... 198/469.1, 471.1, 408, 377.06, 377.08
    See application file for complete search history.

(56) References Cited

U.S. PATENT DOCUMENTS

| | | | |
|---|---|---|---|
| 8,820,513 B2 * | 9/2014 | Papsdorf | A61F 13/15764 198/478.1 |
| 9,475,657 B2 * | 10/2016 | Bettinelli | B65G 47/848 |
| 9,511,952 B1 * | 12/2016 | Schneider | B65G 47/244 |
| 2012/0145314 A1 * | 6/2012 | Piantoni | A61F 13/15764 156/256 |
| 2013/0296148 A1 * | 11/2013 | Schneider | A61F 13/15772 493/3 |
| 2016/0031654 A1 * | 2/2016 | Bettinelli | B65G 29/00 198/377.01 |
| 2016/0130094 A1 | 5/2016 | Albonetti | |
| 2018/0104112 A1 * | 4/2018 | Piantoni | A61F 13/15764 |

FOREIGN PATENT DOCUMENTS

| | | |
|---|---|---|
| CN | 105246804 A | 1/2016 |
| CN | 105431364 A | 3/2016 |
| EP | 0439897 A1 | 8/1991 |
| EP | 2659869 A1 | 11/2013 |
| WO | 2008155618 A2 | 12/2008 |
| WO | 2014167369 A1 | 10/2014 |
| WO | 2015079367 A1 | 6/2015 |

* cited by examiner

APPARATUS FOR TRANSFERRING AND ROTATING AN OBJECT

TECHNICAL FIELD

The present invention relates to an apparatus for transferring and rotating of at least one object, particularly of small dimensions, for example a base component for the production of an absorbent article, between two operating stations that allow changing the orientation of the object between the same stations. In detail, the present invention relates to a transfer and rotation apparatus included in a packaging machine for the realization of sanitary absorbent articles.

BACKGROUND

As is well known, sanitary articles, in particular baby diapers, sanitary napkins or incontinence products for adults comprise a layer of absorbent padding enclosed in a layer of non-woven fabric and a waterproof layer, for example polyethylene. These components are the basic elements of an absorbent article. In addition to these basic components mentioned above, the absorbent articles comprise further additional components (such as elastic bands, fecal barriers and side wings) which make the structure, as well as the realization, complex.

A known type of packaging machine for making sanitary absorbent articles comprises an advancing line of a continuous strip of impermeable material along which a plurality of operating units are disposed which feed the continuous web both of the basic components and of the additional components intended to complete the absorbent article.

Each operating unit comprises a processing apparatus that receives a component and processes the same component (for example by cutting the component into discrete lengths if the component is fed as a continuous strip to the processing apparatus) and a transferring and rotating apparatus that receives the component from the processing apparatus, when the processing has ended, and applies the component to the strip of impermeable material, picking up the component in a first orientation and releasing it in a second orientation, rotated with respect to the first orientation.

Generally, the transferring and rotating apparatus comprises a central drum which rotates around a central axis of rotation and supports, by means of a plurality of radially extending arms, respective suction retaining heads to hold the component during the transfer. Each suction retaining head can rotate further relative to the central drum itself to change the orientation of the component between a pickup station, in which the basic component is received by the transfer element, and a release station, in which the base component is released to a subsequent apparatus.

During the rotation of the central drum, the position of the suction retaining head with respect to a rotation axis of the drum itself is modified radially between a first radius, at the pickup station, and a second radius, at the release station, for varying the linear speed of the retaining head itself, and then accelerate or decelerate the components during the transfer from the pickup station to the release station.

In this way it is possible to pick up a succession of basic components from the pickup station spaced at a certain interval, commonly also called step or "pitch", and deliver the same components in the release station spaced by a different interval.

The rotation of the radial arms with respect to the central drum, the rotation of the retaining heads with respect to the radial arms and the variation of the radial position of each retaining head are mechanically controlled by means of respective driving cams.

The variation of the radial position of each retaining head can cause excessive stresses in the retaining head, and then excessive wear of the same retaining head that may be subject to breakage or undesired malfunctions.

Furthermore, during a format change operation, i.e. during an operation that changes the packaging machine to vary the type of sanitary absorbent articles which are to be packaged, it is often necessary to modify the law of motion of the suction retaining heads to adapt this law of motion to a different size and/or location of the components that are treated.

Modification of the law of motion of the retaining heads requires the replacement of some mechanical components, typically at least the corresponding cams, and such replacement is particularly long and complex due to the positioning of the cams themselves towards the base of the transferring and rotating apparatus, which requires disassembly and subsequent assembly of numerous additional mechanical components and a step of configuration that is rather lengthy and requires the intervention of a skilled technician.

EP 2659869 A1 discloses an apparatus for transferring and rotating an object.

SUMMARY

The object of the present invention is to provide an apparatus for transferring and rotating an object, which is free from the drawbacks described above, and which, in particular, is simple and economical to produce.

A further object is to provide an apparatus for transferring and rotating an object that transfers and rotate an object reducing the possible wear of the mechanical components and which has therefore a longer operating life than the prior art.

According to the present invention, there is provided an apparatus for transferring and rotating an object, as claimed in the attached claims.

BRIEF DESCRIPTION OF THE DRAWINGS

The present invention will now be described with reference to the accompanying drawings which illustrate some exemplifying and not limitative embodiments thereof, in which.

DETAILED DESCRIPTION

In this description, similar elements in common to the embodiments illustrated are indicated with the same numbering.

Figure 9:
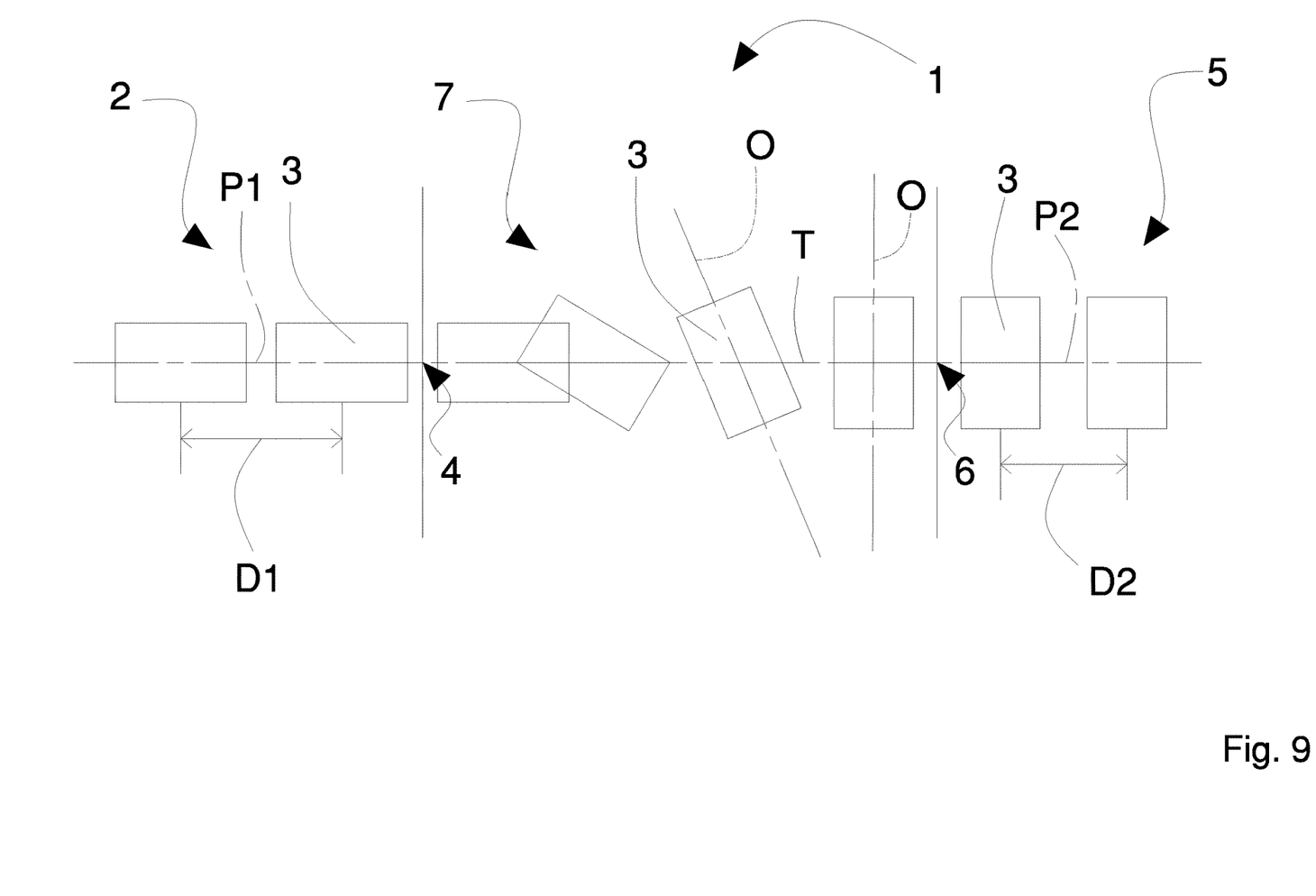
FIG. 9 is a schematic representation of the apparatus of FIGS. 1 to 7, during operation.

As shown in FIG. 9, with 1 is indicated in its entirety a packaging machine for the production of hygiene articles. The packaging machine 1 comprises a processing apparatus 2 which feeds to a retaining station 4, in succession and along a processing path P1 a plurality of objects 3, in particular components or additional components for the construction of hygienic articles. Details on the processing apparatus 2 and the components for making sanitary articles have already been provided previously and will not be herein repeated.

The packaging machine 1 also comprises an advancing line 5 of a continuous strip (not shown) of impermeable material which receives in succession the objects 3 from a releasing station 6 and moves them along a feed path P2.

Note that the objects 3 have a first orientation in the retaining station 4 which is different from a second orientation in the releasing station 6.

Assuming that each object has a longitudinal axis O, or an axis of prevalent development O, the first orientation is given by the arrangement of the longitudinal axis O with respect to the processing path P1 and the second orientation is given by the arrangement of the longitudinal axis O with respect to the feed path P2.

In the retaining station 4, the objects 3 have their longitudinal axis O parallel to the feed path P1, and are spaced apart by a distance D1 while in the release station 6 the longitudinal axis O of each object 3 is perpendicular to the path of advancement P2 and the objects 3 are rotated and spaced apart by a distance D2.

The packaging machine 1 comprises a transferring and rotating apparatus 7 for the transfer and the rotation of at least one object 3 from the retaining station 4 to the releasing station 6 along an annular transfer path T.

As shown in detail in FIGS. 1 to 8, the transferring and rotating apparatus 7 comprises a stator 8 (FIG. 6) comprising a revolution body 24, provided with a lateral surface 25, and a rotor 9 (FIGS. 1, 2, 3 and 7) rotatable about a first axis R1 of rotation relative to the stator 8.

The rotor 9 comprises at least one retaining head 10 of the object 3 connected to the rotor 9, which retaining head 10 comprises a respective retaining element 11 rotatable about a second axis of rotation R2 (FIG. 5) with respect to the same rotor 9. The retaining head 10 receives the object 3 in the retaining station 4 from the processing apparatus 2, and transfers the object 3 to the releasing station 6 of the advancing line 5 along the transfer path T rotating the object 3 from the first orientation to the second orientation during the rotation the rotor 9.

The retaining element 11 is shaped such as to be able to cooperate with the object 3. In the embodiment shown in FIGS. 1 to 7, the retaining element 11 is externally convex and presents surface openings 11a to allow the retention and the transport of the object by means of air suction devices, known and not illustrated. In other words, the retaining head 10 is a retaining suction head.

The stator 8 includes a first cam profile 12 (FIG. 6) being realized in the side surface 25 and the retaining head 10 is provided with a corresponding first follower 13, for example a roller, which cooperates and is coupled to the first cam profile 12. The first follower 13 is suitable to cause the rotation of the retaining element 11 around the second rotation axis R2 as a function of the relative position of the first follower 13 relative to the first cam profile 12.

The stator 8 also comprises a second cam profile 14, of which further details are in the following.

As shown in FIGS. 1 to 7, the transferring and rotating apparatus 7 comprises at least a first annular guide 15 arranged along the transfer path T and the retaining head 10 comprises at least a first slide 16 that supports the retaining element 11 and is slidably coupled to the first annular guide 15.

The first slide 16 is connected to the rotor 9 by means of a respective variation mechanism 17 of the angular position of the retaining head 10 with respect to the rotor 9, which variation mechanism 17 cooperates and is coupled to the second cam profile 14 to cause the sliding of the first slide 16 in the first annular guide 15, as a function of the relative position of the variation mechanism 17 with respect to the second cam profile 14.

The first annular guide 15 is fixed to the rotor 9 and is rotatable with respect to the stator 8 integrally with the rotor 9.

The variation mechanism 17 oscillates with respect to a rotation pivot 18, having a third rotation axis R3 which is parallel to the first rotation axis R1 of the rotor 9. The variation mechanism 17 has a first end 17a which is provided with a second follower 19, for example a roller as in the attached figures, suitable to be coupled to the second cam profile 14, and a second end 17b which is fastened to the first slide 16.

Note that the variation mechanism 17 comprises a substantially triangular plate and that the rotation pivot 18 is placed at a vertex, the first end 17a and second end 17b of the variation mechanism 17 being located at respective ends of a respective first arm and second arm extending from the vertex.

The stator 8 also comprises a front wall 22 and the second cam profile 14 comprises a flat cam being realized by means of a groove of the front wall 22.

The transferring and rotating apparatus 7 comprises a motor 23 (FIGS. 1 and 2), which is placed beyond a pedestal of the apparatus and is connected in known manner to the rotor 9 by means of drive gears.

Figure 6:
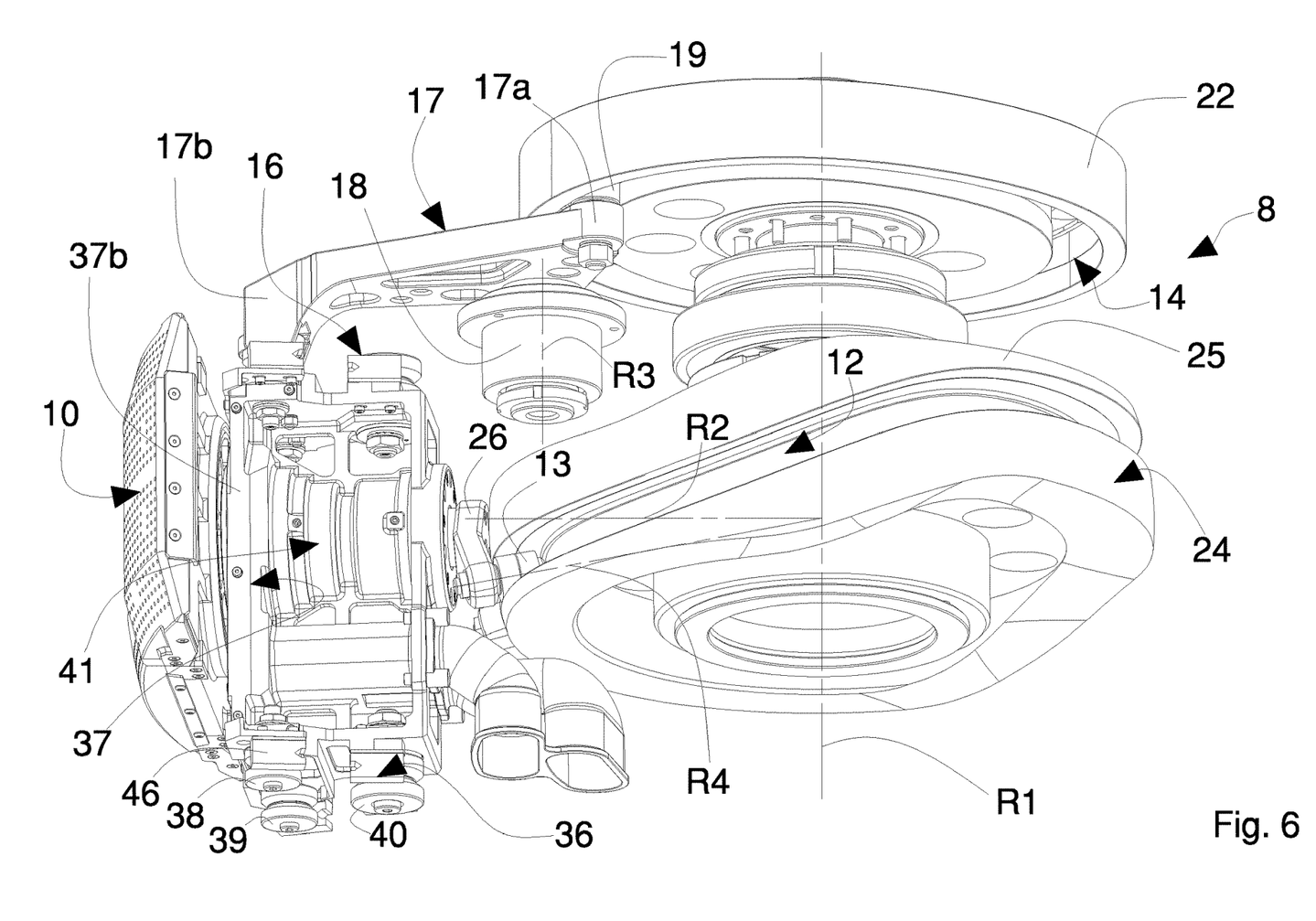
FIG. 6 is a rear perspective view of the retaining head of FIGS. 4 and 5, and of a first cam and a second cam of the transferring and rotating apparatus of FIG. 1, with parts removed for clarity.

The revolution body 24 of the stator 8, shown in detail in FIG. 6, is so shaped as to be sphere-conic, i.e. it has a spherical surface that is tapered at the ends with an axis of symmetry which corresponds to the first rotation axis R1 of the rotor 9.

Note that the first cam follower 13, which extends axially along a fourth rotation axis R4, is connected via a lever 26, which has two portions which are inclined one another, to a rotation shaft 41 (FIG. 6) which extends between a first end, connected to the lever 26 itself, and a second end (not shown), to which is fastened the retaining element 11. The rotation shaft 41 is rotatable with respect to the second rotation axis R2 so that to every movement of the first follower 13 in the respective first cam profile 12 follows a corresponding rotation of the retaining element 11 about its own second rotation axis R2.

The second rotation axis R2 of the retaining element 11 and the fourth rotation axis R4 of the first cam follower 13 are incident to each other and incident also, in a point of incidence, to the first rotation axis R1 of the rotor 9.

This is due to the particular shape of the revolution body 24 and of the lever 26, the former being of frustum-shaped type and the latter having portions inclined one to the other.

In detail, the revolution body 24, the first cam profile 12 and the first follower 13, the particular mutual arrangement between the first rotation axis R1 of the rotor 9, the second rotation axis R2 of the retaining element 11 and the fourth rotation axis R4 of the first follower 13 are of a known type as shown by the International application WO2014/167369 which is cited and incorporated herein without loss of generality.

Figure 8:
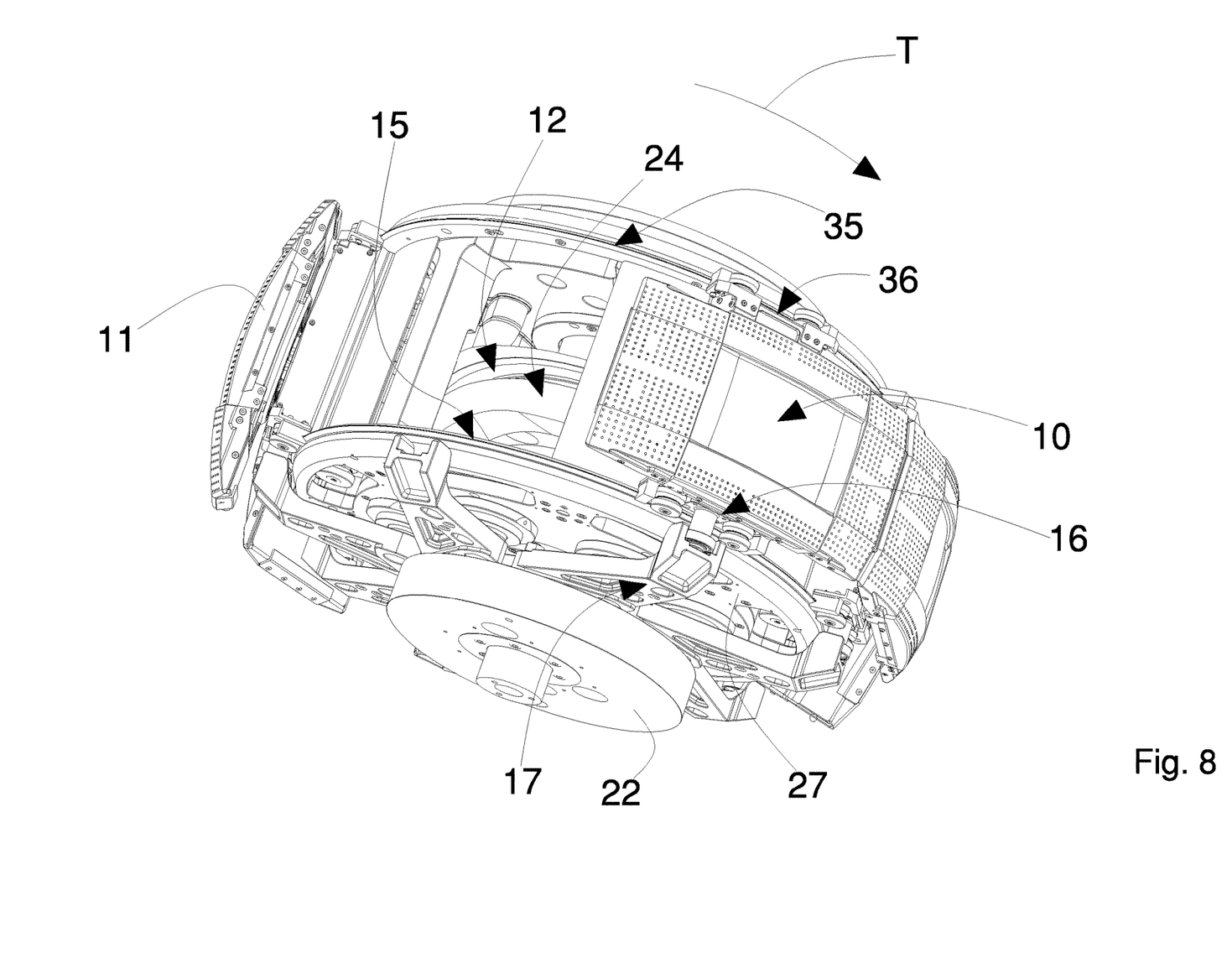
FIG. 8 is a perspective view of another portion of the transferring and rotating apparatus of FIG. 1, with a retaining head removed for clarity in order to highlight an arrangement of a revolution body between the two annular guides of FIGS. 4 and 5.

As shown in FIG. 8, the rotor 9 may comprise, in particular, a body 27, interposed between the revolution body 24 and the front wall 22. The body 27 may be circular. The first annular guide 15 is interposed between the body 27 and the revolution body 24.

Figure 1:
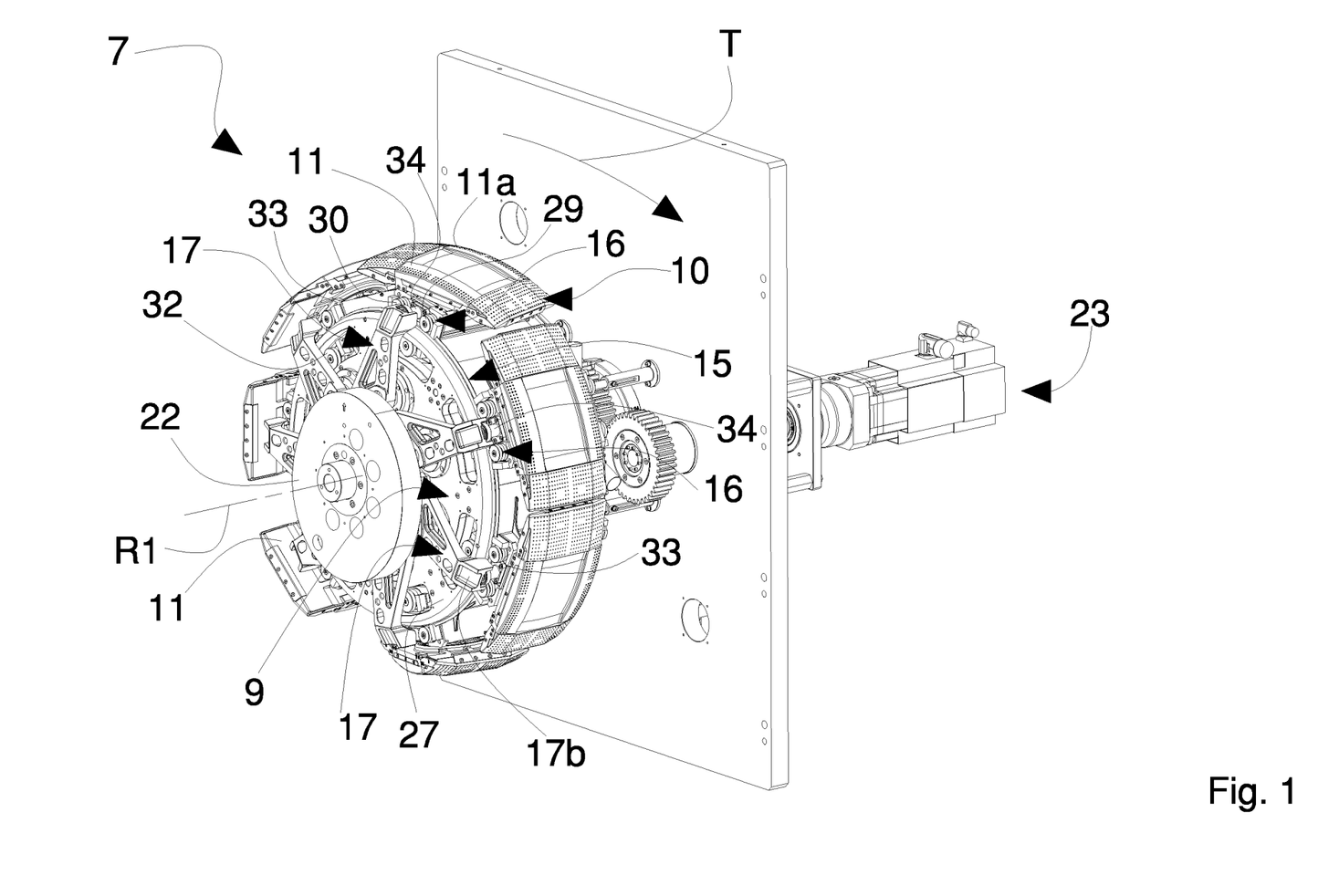
FIG. 1 is a front perspective view of a transferring and rotating apparatus according to the invention.
Figure 2:
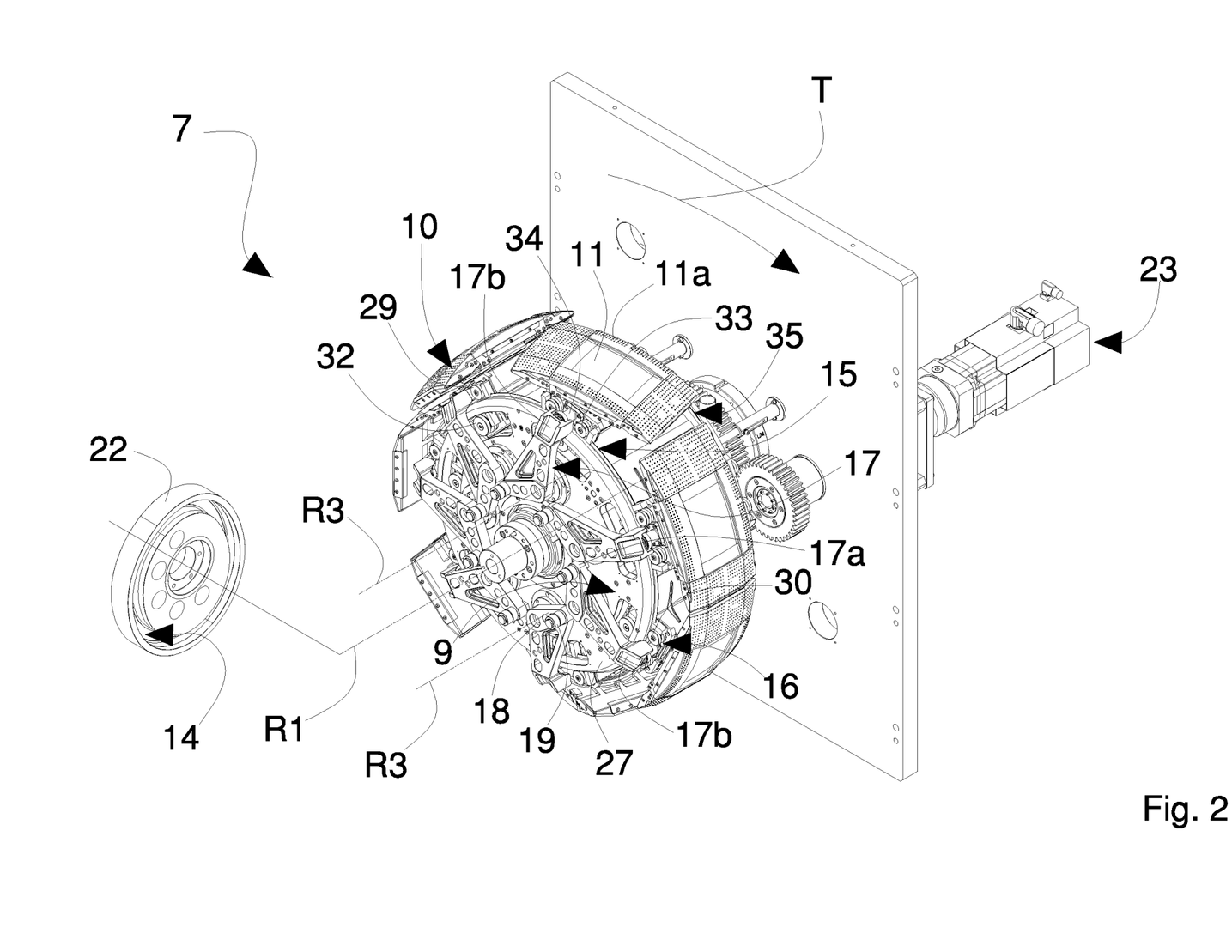
FIG. 2 is a front perspective view of the transferring and rotating apparatus of FIG. 1, in which a front wall is rotated for clarity.
Figure 3:
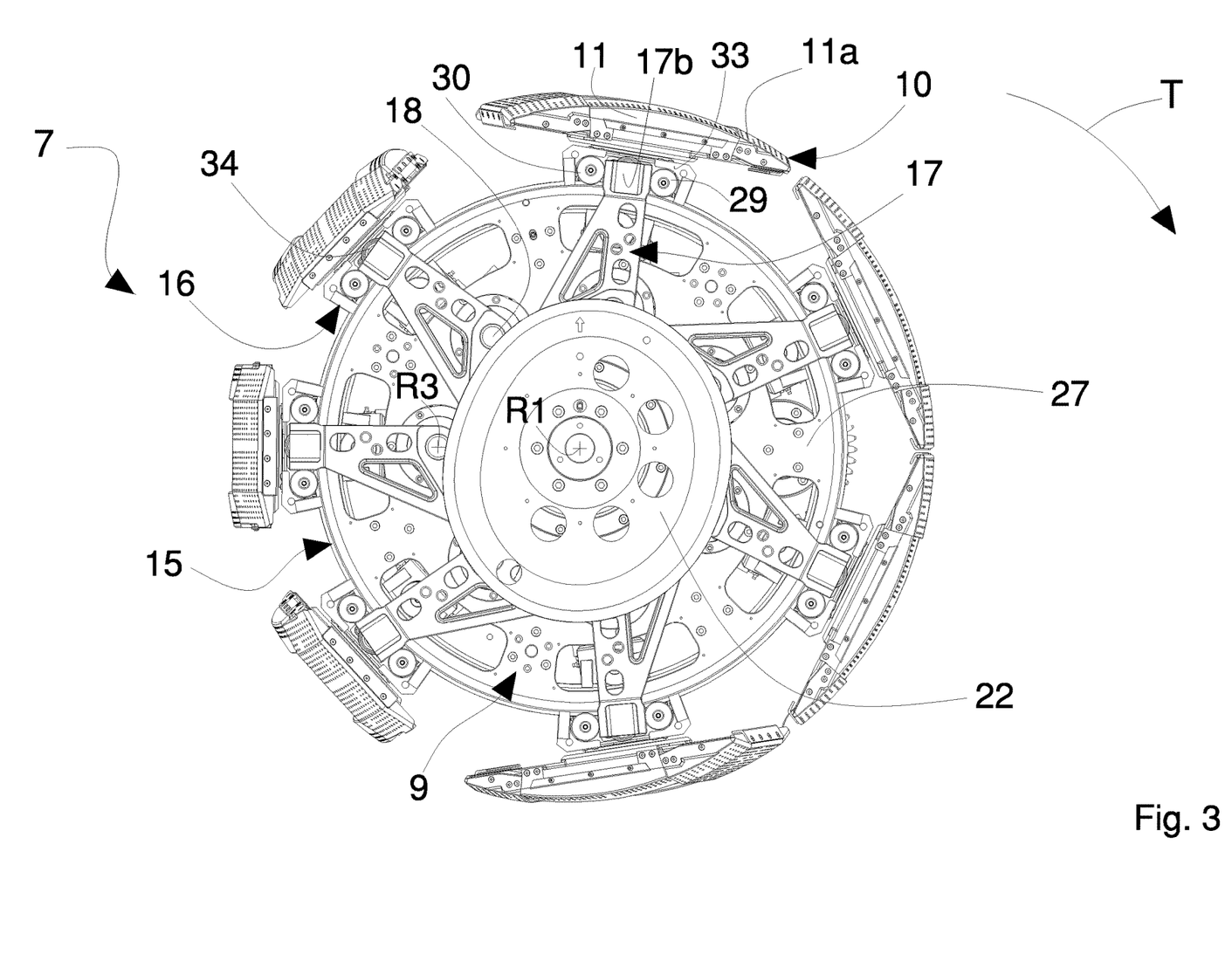
FIG. 3 is a front view of the transferring and rotating apparatus of FIG. 1.
Figure 4:
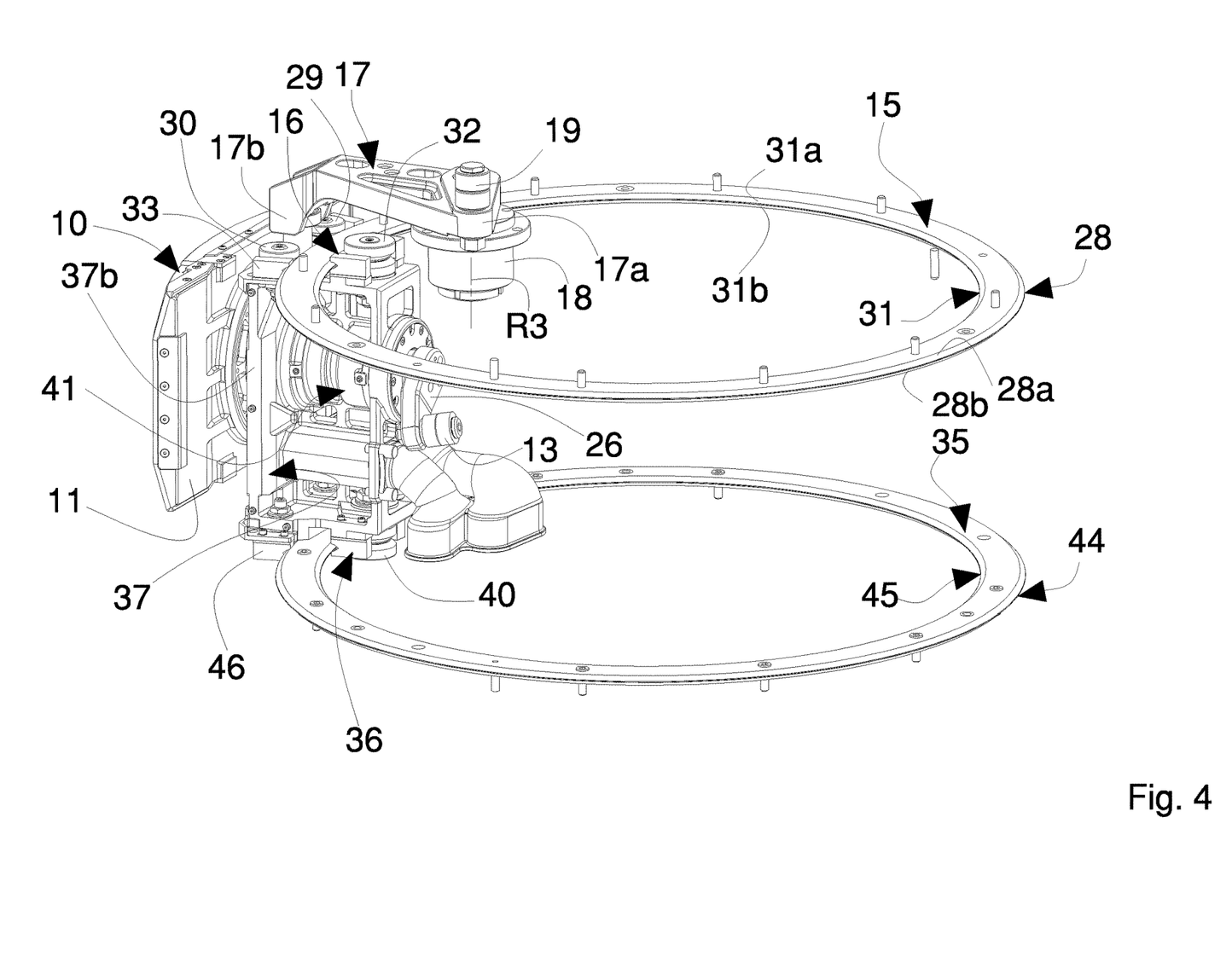
FIG. 4 is a first perspective view of a retaining head and two annular guides of the transferring and rotating apparatus of FIG. 1, which annular guides slidingly support the retaining head, with parts removed for clarity.
Figure 5:
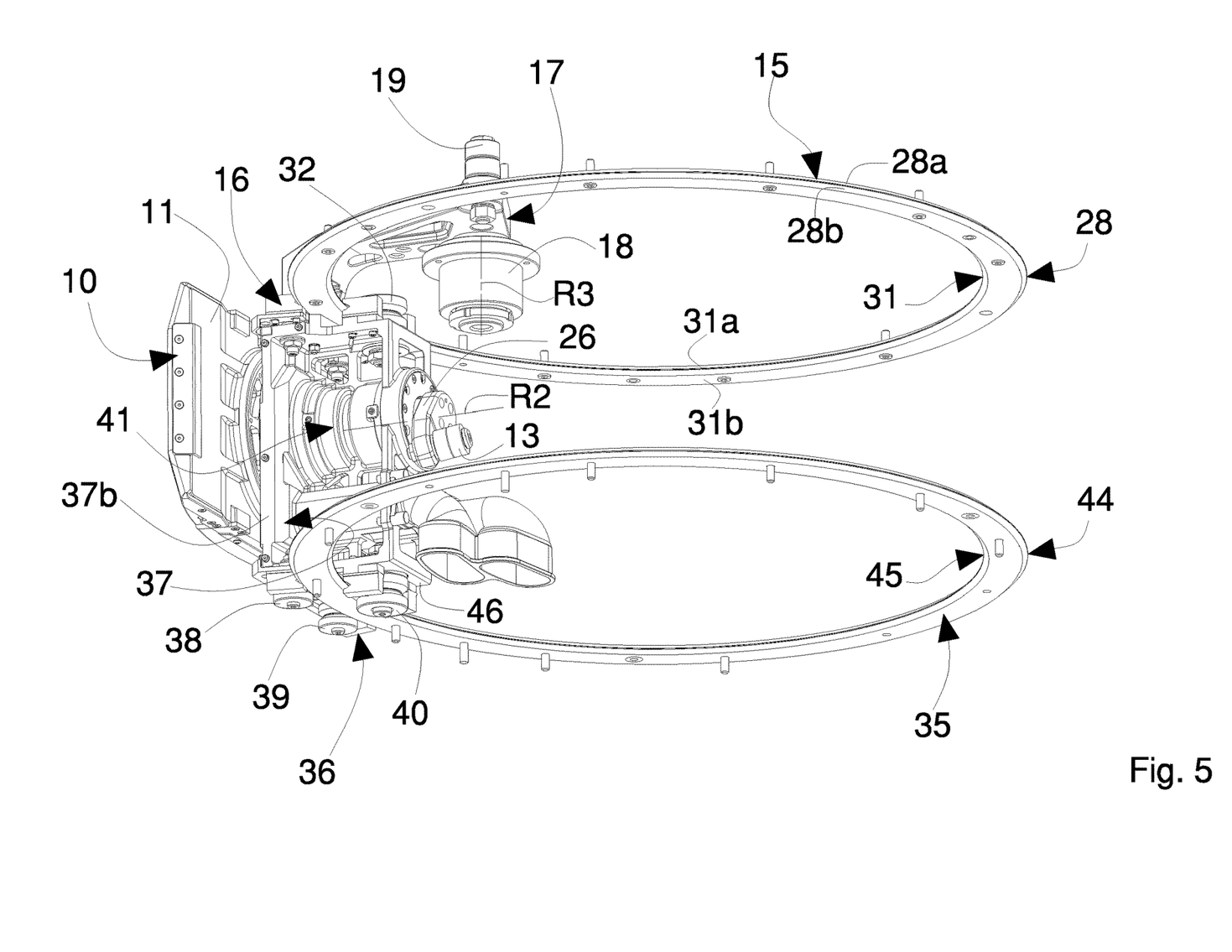
FIG. 5 is a second perspective view of the retaining head and of two annular guides of FIG. 4.

More in detail, as shown in FIGS. 4 and 5, the first annular guide 15 comprises an external edge 28, in particular having V-section, which is provided with two respective rolling surfaces 28a and 28b opposite to each other. The first slide 16 comprises a first pair of wheels 29 and a second pair of wheels 30, being spaced from each other along the transfer path T, which are idly mounted on the first slide 16 such as to slide on the external edge 28. The first pair of wheels 29 is downstream of the second pair of wheels 30 along the transfer path T. The wheels of each pair of wheels 29 and 30 are coaxially arranged in order to roll each along a respective rolling surface 28a and 28b of the external edge 28 of the first annular guide 15.

In addition, the first annular guide 15 also includes an internal edge 31, having a smaller distance than the external edge 28 with respect to the first rotation axis R1 of the rotor 9, which is also provided with two respective rolling surfaces 31a, 31b opposite to each other. The first slide 16 comprises, in addition, a third pair of wheels 32 which are idly mounted on the first slide 16 such as to slide on the internal edge 31. The wheels of the third pair 32 are coaxial to each other and are arranged in order to roll, each, along a respective rolling surface 31a, 31b of the internal edge 31.

The wheels of the third pair 32 are interposed between the first pair of wheels 29 and the second pair of wheels 30 along the transfer path T. The arrangement of the wheels of the first pair 29, the second pair 30, and the third pair 32 at the vertexes of a triangle facing towards the first rotation axis R1 of the rotor 9 in which the wheels of the third pair 32 define a vertex, ensure a simultaneous sliding of the slide 16 both on the external edge 28 and on the internal edge 31, and then an optimal stability of the first slide 16 during the sliding.

The first slide 16 comprises a respective bracket 33 on which the first pair of wheels 29, the second pair of wheels 30 and the third pair of wheels 32 are fastened, the first pair of wheels 29 and the second pair of wheels 30 being fastened more outwardly with respect to the third pair of wheels 32 with respect to the first rotation axis R1 of the rotor 9.

Note in addition that the first slide 16 comprises a fastening pin 34, which fastening pin 34 has a first end fastened to the bracket 33 and a second end secured to the second end 17b of the variation mechanism 17.

The fastening pin 34 is interposed between the first pair of wheels 29 and the second pair of wheels 30 along transfer path T, in such a way that the said second end 17b is fixed in a substantially central position in the first slide 16 in order to ensure optimal sliding.

The transferring and rotating apparatus 7 also comprises a second annular guide 35 and it is noted that the revolution body 24 of the stator 8 is interposed between the first annular guide 15 and the second annular guide 35.

The retaining head 10 also comprises a second slide 36 (FIGS. 4, 5, 6 and 7), which supports the retaining element 11 and is slidably coupled to the second annular guide 35; in addition the retaining head 10 also comprises a supporting base 37, in particular rectangular, at whose first opposite sides 37a the first slide 16 and the second slide 36 are respectively fixed.

The second annular guide 35 is similar to the first annular guide 15 as well as the second slide 36 is similar to the first slide 16.

A first pair of wheels 38 and a second pair of wheels 39 of the second slide 36 are then idly mounted on the second slide 36 to slide on an external edge 44 of the second annular guide 35 while a third pair of wheels 40 is idly mounted on the second slide 36 to slide on an internal edge 45 of the second annular guide 35. The only difference between the first slide 16 and second slide 36 is given by the absence in the second slide 36 of the fastening pin 34 of the change mechanism 17.

The second slide 36 comprises a respective bracket 46 on which are fixed the first pair of wheels 38, the second pair of wheels 39 and the third pair of wheels 40, the first pair of wheels 38 and the second pair of wheels 39 being fixed more outwardly with respect to the third pair of wheels 40 with respect to the first rotation axis R1 of the rotor 9, in a similar manner to what already said for the first slide 16.

The bracket 33 of the first slide 16 and the bracket 46 of the second slide 36 are fixed laterally to first opposite sides 37a of the supporting base 37.

In this way, the supporting base 37, the first slide 16 and the second slide 36 define a support carriage of the retaining element 11 which is slidable on the first annular guide 15 and on the second annular guide 35.

Figure 7:
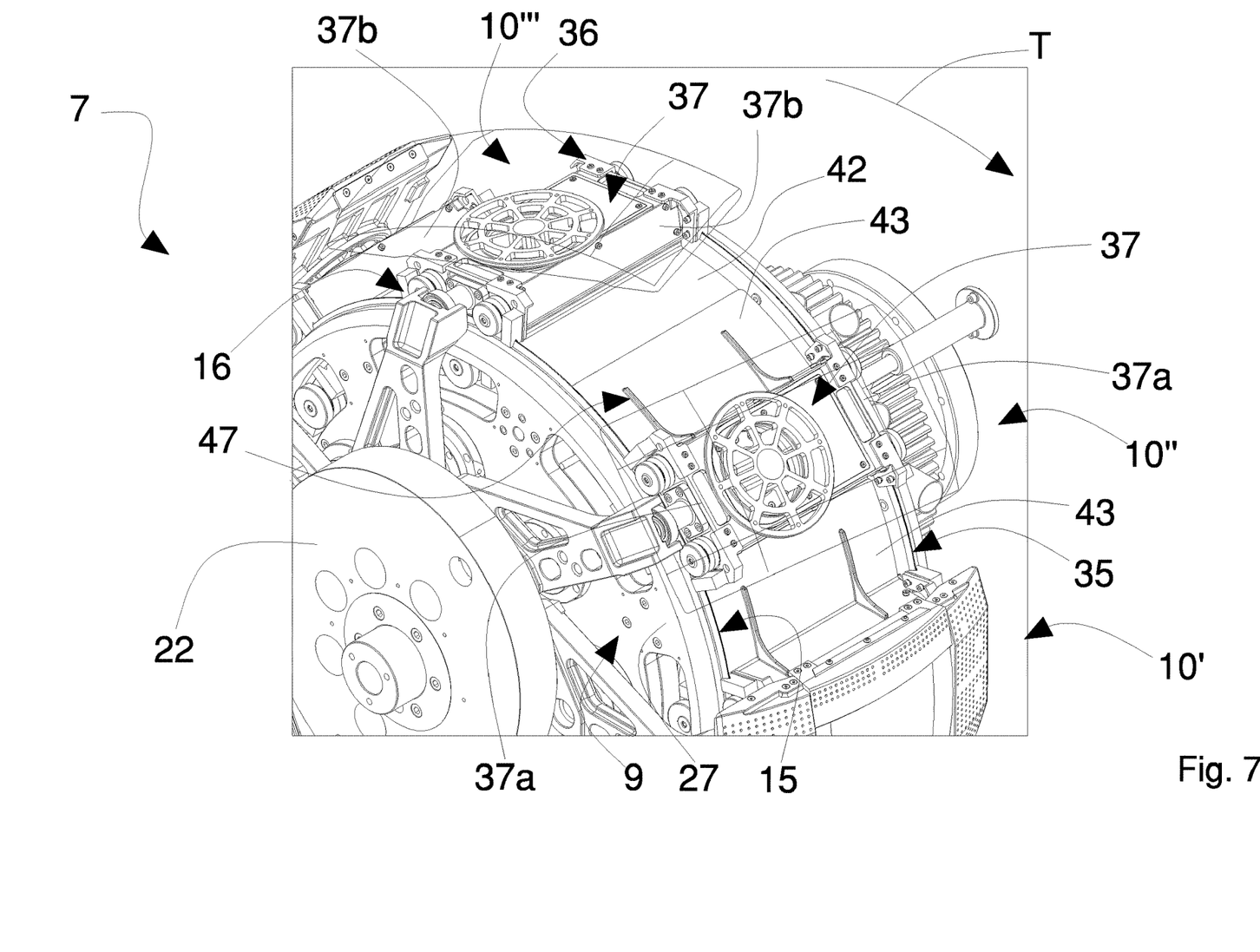
FIG. 7 is a perspective view of a portion of the transferring and rotating apparatus of FIG. 1, in which in each retaining head respective retaining elements are represented as transparent, to highlight a respective support carriage of the retaining element.

As is shown in detail in FIG. 7, the support base 37 has a hole in order to house a rotation shaft 41 to which the retaining element 11 is fixed. The rotation shaft 41 extends axially along the second axis of rotation R2 of the retaining element 11 and is fixed to the supporting base 37 via annular bearings that allow the rotation shaft 41, integral with retaining element 11, to be able to rotate with respect to the supporting base 37.

As shown in FIG. 7, the retaining head 10 comprises a first protective wall 42 and a second protective wall 43 fastened to second opposite sides 37b of the supporting base 37, respectively downstream and upstream from the support base 37 along transfer path T. Protective walls 42 and 43 are configured to protect the first cam profile 12 from contaminants and particles, in detail each comprises a first portion that overlaps a side of the supporting base 37b and a second portion that overlaps the first cam profile 12. For the attachment of the protective walls 42 and 43 to the supporting base 37 suitable fastening supports are present, among which the supports for the attachment of the protective wall 43 are external, shaped to "L" and indicated with 47 in FIG. 7.

Note that the transferring and rotating apparatus 7 shown in the Figures comprises a plurality of retaining heads 10, in detail comprises seven different retaining heads, which are radially distributed about the first axis of rotation R1 of the rotor 9.

If we consider two successive retaining heads, namely a first retaining head which is downstream of a second retaining head along the transfer path T, it can be observed that the first retaining head and the second retaining head are able to be spaced from each other in a distanced position or in a near position depending on the relative position of the respective variation mechanisms with respect to the second cam profile 14.

The first protective wall 42 and the second protective wall 43 of each support base 37 are fastened with an offset in a radial direction with respect to the first rotation axis R1 of the rotor 9 so that, the first protective wall 42 of the upstream retaining head and the second protective wall 43 of the downstream retaining head are superimposed when two successive retaining heads are in a near position.

This is particularly evident in FIG. 7, in which three subsequent retaining heads 10', 10" and 10''' are represented, each identified with a respective apices for simplicity, of which the most downstream retaining head 10' is in a near position with respect to the central retaining head 10" and the central retaining head 10" is in a distanced position with respect to the most upstream retaining head 10'''.

Note that the second protective wall 43 of the downstream retaining head 10' is superimposed on the first protective wall 42 of the central retaining head 10" while the second protective wall 43 of the central retaining head 10" is distanced and not superposed on the first protection wall 42 of the most upstream retaining head.

In use, when the motor 23 puts the rotor 9 in operation, all the retaining heads 10 with which the transferring and rotating apparatus 7 is fitted are all at the same distance and the rotation pivot 18 of the variation mechanism 17 of each retaining head 10 moves at the same angular speed of the rotor 9. The second follower 19 moves, however, engaging the second cam profile 14 of the front wall 22, which is eccentric with respect to the first rotation axis R1 of the rotor 9, and then the variation mechanism 17 periodically rotates by a certain angle with respect to the rotor 9 as a function of the relative position of the second follower 19 with respect to the second cam profile 14. During the rotation of the rotor 9, the second end 17b of the variation mechanism 17 moves then periodically forward and consequently drags forward also the first slide 16, integral with the variation mechanism 17 by means of the fastening pin 34.

It follows that, cyclically, each retaining head 10 is accelerated and subsequently decelerated. Considering two successive retaining heads then the distance between them can be modified during rotation of the rotor 9 about the first rotation axis R1 and therefore the distance D1 (pickup step) between two successive retaining heads at the retaining station 4, can be different from the distance D2 (release step) between two successive retaining heads at the releasing station 6.

The sliding of the first slide 16 also drags the carriage, defined by the first slide 16 itself, the support base 37 and the second slide 36, and the carriage in turn drags the rotation shaft 41 and the retaining element 11, that moves integrally to the carriage. Since one end of the rotation shaft 41 is connected to the first follower 13 which moves during the rotation of the rotor 9 by engaging the first cam profile 12 of the revolution body 24, which is also eccentric with respect to the first rotation axis R1 of the rotor 9, the retaining element 11 fixed to the other end of the rotation shaft 41 rotates with respect to the second rotation axis R2 as a function of the position of the first follower 13 in the first cam profile 12.

The first cam profile 12 and the second cam profile 14 are shaped in such a way that each retaining head 10 can be accelerated before being rotated by 90°.

Owing to the retaining head 10 connected to the rotor 9 via a respective variation mechanism 17 of the angular position and owing to the support of the retaining element 11 by means of a first slide 16 slidably coupled to a first annular guide 15, which rotates integral to the rotor 9, the retaining head 10 is supported in a sturdy manner and also is driven with stable movements to transfer and rotate an object, i.e. a component of a hygienic article.

It is added that the presence of both the first annular guide 16 and the second annular guide 36, on which the second slide 35 slides, allows a carriage defined by the support base 37, by the first slide 16 and by the second slide 36, to slidably support the rotation shaft 41, to which the retaining element 11 is fixed, avoiding possible vibrations to the retaining element 11 itself during its rotation about the second axis of rotation R2. Consequently it is guaranteed stability in the transport of components of sanitary items, usually lightweight and easily deformable.

The specific arrangement of the revolution body 24 between the first annular guide 16 and the second annular guide 36 and the arrangement of the second cam profile 14 in a front wall 22 of the stator 8 which is directed, in use, toward the operator side, allows a simple variation of the picking up step and the release step where it is necessary a format change.

It is possible to modify a format of the transferred component by changing the number of retaining heads 10, since the retaining elements 11 can consequently be replaced, to change their shape and/or size. By only replacing the front wall 22 in which the second cam profile 14 is obtained, it is possible that an operator changes the law of motion of any new retaining heads without difficult setup configurations, such as to decide acceleration and/or deceleration areas different from the previous format.

The invention claimed is:

1. An apparatus for transferring and rotating an object from a retaining station to a releasing station along an annular transfer path, wherein the object has a first orientation in the retaining station which is different from a second orientation in the releasing station, wherein the apparatus comprises:
   a stator including a revolution body provided with a lateral surface;
   a rotor being rotatable about a first rotation axis with respect to the stator;
   at least one retaining head of the object connected to the rotor and including a retaining element being rotatable about a second rotation axis with respect to the rotor;
   at least one first annular guide being arranged along the transfer path;
   and wherein:
   the stator includes a first cam profile being realized in said lateral surface and the retaining head includes a corresponding first follower cooperating and being coupled to the first cam profile, the first follower being suitable to cause the rotation of the retaining element about the second rotation axis as a function of the relative position of the first follower with respect to said first cam profile;
   the stator includes a second cam profile;
   the retaining head includes at least one first slide that supports the retaining element and that is slidingly coupled to the first annular guide;

the first slide is connected to the rotor by a mechanism provided with a second follower being adapted to be coupled to the second cam profile to cause the sliding of the first slide in the first annular guide as a function of the relative position of the mechanism with respect to said second cam profile;

the stator includes a front wall on which the second cam profile is realized; and the rotor includes a circular body being interposed between the revolution body and the front wall.

2. The apparatus according to claim 1, wherein said mechanism is a mechanism for variating the angular position of said retaining head with respect to the first rotation axis of said rotor.

3. The apparatus according to claim 1, wherein said mechanism is oscillating with respect to a rotation pivot that is carried by the rotor and has a third rotation axis being parallel to the first rotation axis of the rotor, said mechanism having a first end provided with said second follower and a second end fastened to the first slide.

4. The apparatus according to claim 1, wherein the second cam profile includes a flat cam being realized by means of a groove of said front wall.

5. The apparatus according to claim 1, wherein the first annular guide is interposed between said circular body and the revolution body.

6. The apparatus according to claim 1, wherein the first annular guide is interposed between the circular body and the front wall.

7. The apparatus according to claim 1, wherein the first annular guide includes an external edge, which is provided with two respective rolling surfaces being opposite to each other, and wherein the first slide includes a first pair of wheels and a second pair of wheels being spaced from each other along the transfer path, which are idly mounted on the first slide, the wheels of each pair being coaxially arranged in order to roll each along a respective rolling surface of the external edge of the first annular guide.

8. The apparatus according to claim 7, wherein the first annular guide, also includes an internal edge, having a smaller distance than the external edge with respect to the first rotation axis of the rotor, which is also provided with two respective rolling surfaces being opposite to each other, and wherein the first slide includes a third pair of wheels which are idly mounted on the first slide, coaxial to each other and each arranged in order to roll along a respective rolling surface of the internal edge; the third pair of wheels being interposed between the first pair of wheels and the second pair of wheels along the transfer path.

9. The apparatus according to claim 8, wherein the first slide includes a bracket on which the first pair of wheels, the second pair of wheels and the third pair of wheels are fastened, the first pair of wheels and the second pair of wheels being fastened more outwardly with respect to the third pair of wheels with respect to the first rotation axis of the rotor.

10. The apparatus according to claim 9, wherein the first slide also includes a respective fastening pin, which pin has a first end being fastened to the bracket and a second end being fastened to an end of said mechanism.

11. The apparatus according to claim 1, and further comprising a second annular guide, the revolution body being interposed between the first annular guide and the second annular guide; and wherein the retaining head also includes a second slide that supports the retaining element and that is slidingly coupled to the second annular guide.

12. The apparatus according to claim 11, wherein the retaining head includes a supporting base, particularly a rectangular one, at whose first opposite sides the first slide and the second slide are respectively fastened; the supporting base having a hole in order to house a shaft extending between a first end, to which the first follower is connected, and a second end, to which the retaining element is connected.

13. The apparatus according to claim 12, wherein the supporting base, the first slide and the second slide define a supporting carriage of the retaining element which is slidable on the first annular guide and the second annular guide.

14. The apparatus according to claim 13, wherein the retaining head includes a first protective wall and a second protective wall being fastened to second opposite sides of the supporting base, respectively downstream and upstream from the supporting base along the transfer path, which protective walls are configured to protect the first cam profile from contaminating particles.

15. The apparatus according to claim 14, and comprising a plurality of retaining heads among which a first retaining head is downstream from a second retaining head along the transfer path; the first retaining head and the second retaining head being able to be spaced from each other in a distanced position or in a near position depending on the relative position of the respective mechanisms with respect to the second cam profile; the first protective wall and the second protective wall of each supporting base being fastened with an offset in a radial direction with respect to the first rotation axis of the rotor so that, when the first retaining head and the second retaining head are in the near position, the first protective wall of the second retaining head and the second protective wall of the first retaining head are superimposed one to the other.

16. The apparatus according to claim 1, wherein the first follower extends axially along a fourth rotation axis and wherein the second rotation axis of the retaining element and said fourth rotation axis are incident to each other and also incident, in a point of incidence, to the first rotation axis of the rotor.

17. A packaging machine for making sanitary items, wherein the packaging machine comprises:
a processing apparatus successively feeding a plurality of objects, particularly component parts to realize hygiene items, along a processing path to a retaining station, the objects being arranged in the retaining station in a first orientation;
an advancing line of an impermeable material continuous web along an advancing path successively receiving the objects from a releasing station, the objects being received in the releasing station arranged in a second orientation;
wherein the packaging machine also includes the transferring and rotating apparatus according to claim 1, the transferring and rotating apparatus including at least one retaining head in order to receive an object from the retaining station of the processing apparatus and to transfer the object itself to the releasing station of the advancing line along a transfer path by rotating it from the first orientation to the second orientation.

18. The apparatus according to claim 2, wherein said mechanism is oscillating with respect to a rotation pivot that is carried by the rotor and has a third rotation axis being parallel to the first rotation axis of the rotor, said mechanism having a first end provided with said second follower and a second end fastened to the first slide.

19. The apparatus according to claim 2, wherein the second cam profile includes a flat cam being realized by means of a groove of said front wall.

20. The apparatus according to claim 2, and further comprising a second annular guide, the revolution body being interposed between the first annular guide and the second annular guide; and wherein the retaining head also includes a second slide that supports the retaining element and that is slidingly coupled to the second annular guide.

* * * * *